United States Patent
Amala et al.

(10) Patent No.: US 11,498,902 B2
(45) Date of Patent: Nov. 15, 2022

(54) PROCESS FOR THE PREPARATION OF CABOZANTINIB AND ITS PHARMACEUTICALLY ACCEPTABLE SALTS THEREOF

(71) Applicant: NATCO PHARMA LIMITED, Hyderabad (IN)

(72) Inventors: Kompella Amala, Hyderabad (IN); Gampa Venugopala Krishna, Hyderabad (IN); Annadasu Ankamanayudu, Hyderabad (IN); Ganganamoni Srinivasulu, Hyderabad (IN); Konakanchi Durga Prasad, Hyderabad (IN); Muddasani Pulla Reddy, Hyderabad (IN); Nannapaneni Venkaiah Chowdary, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 35 days.

(21) Appl. No.: 16/972,472

(22) PCT Filed: Jun. 4, 2019

(86) PCT No.: PCT/IN2019/050432
§ 371 (c)(1),
(2) Date: Dec. 4, 2020

(87) PCT Pub. No.: WO2019/234761
PCT Pub. Date: Dec. 12, 2019

(65) Prior Publication Data
US 2021/0188776 A1   Jun. 24, 2021

(30) Foreign Application Priority Data
Jun. 5, 2018   (IN)   ............................ 201841021025

(51) Int. Cl.
*C07D 215/233*   (2006.01)

(52) U.S. Cl.
CPC ...... *C07D 215/233* (2013.01); *C07B 2200/13* (2013.01)

(58) Field of Classification Search
CPC ........................ C07D 215/233; C07B 2200/13
See application file for complete search history.

(56) References Cited

U.S. PATENT DOCUMENTS

| | | | |
|---|---|---|---|
| 7,579,473 B2 | 8/2009 | Bannen et al. | |
| 8,877,776 B2 * | 11/2014 | Brown | C07D 215/22 514/312 |
| 2016/0022662 A1 * | 1/2016 | DeCillis | A61K 31/194 514/312 |

FOREIGN PATENT DOCUMENTS

| WO | WO-2005/030140 | 4/2005 |
|---|---|---|
| WO | WO-2014/165786 | 10/2014 |

* cited by examiner

*Primary Examiner* — Timothy R Rozof
(74) *Attorney, Agent, or Firm* — Mintz, Levin, Cohn, Ferris, Glovsky and Popeo, P.C.

(57) ABSTRACT

The present invention relates to an improved process for the preparation of N-(4-(6,7-dimethoxyquinolin-4-yloxy)phenyl)-N'-(4-fluorophenyl)cyclopropane-1,1-dicarboxamide compound of formula-1 which is represented by the following structural formula:

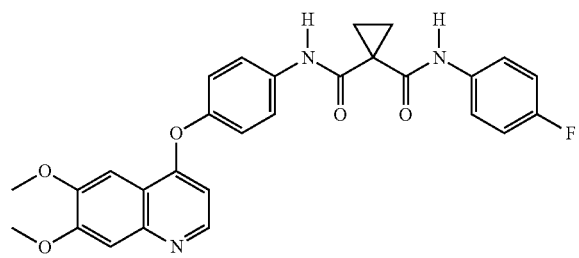

Formula-1

8 Claims, No Drawings

PROCESS FOR THE PREPARATION OF CABOZANTINIB AND ITS PHARMACEUTICALLY ACCEPTABLE SALTS THEREOF

CROSS-REFERENCE TO RELATED APPLICATIONS

This application is a U.S. National Phase Application of PCT International Application No. PCT/IN2019/050432, filed Jun. 4, 2019, which is an International Application of and claims the benefit of priority to Indian Patent Application No. 201841021025, filed Jun. 5, 2018, each of which is incorporated herein in their entirety for all purposes.

FIELD OF THE INVENTION

The present invention relates to an improved process for the preparation of N-(4-(6,7-dimethoxyquinolin-4-yloxy) phenyl)-N'-(4-fluorophenyl)cyclopropane-1,1-dicarboxamide compound of formula-1 which is represented by the following structural formula:

Formula-1

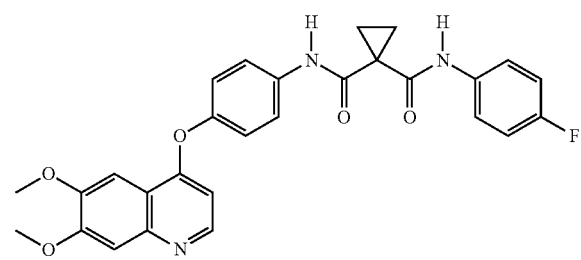

BACKGROUND OF THE INVENTION

Cabozantinib (S)-malate, chemically known as N-(4-(6, 7-dimethoxyquinolin-4-yloxy)phenyl)-N'-(4-fluorophenyl) cyclopropane-1,1-dicarboxamide(S)-malate. Cabozantinib is marketed under the trade name of COMETRIQ® by Exelixis, Inc. COMETRIQ® is indicated for the treatment of patients with progressive, metastatic medullary thyroid cancer.

WO 2005/030140 the corresponding US equivalent U.S. Pat. No. 7,579,473B2 disclosed Cabozantinib or its pharmaceutical acceptable salts thereof. Further it describes a process for the preparation of Cabozantinib, which comprising of reacting 4-aminophenol with 1-(4-fluoro-phenylcarbamoyl)-cyclopropane carboxylic acid in presence of EDCl in DMA to form cyclopropane-1,1-dicarboxylic acid (4-fluoro-phenyl)-amide(4-hydroxy-phenyl)-amide. Further, reacting it with trifluoro methanesulfonic acid 6,7-dimethoxy-quinolin-4-yl ester in presence of anhydrous 2,6-lutidine to give Cabozantinib. The synthetic process disclosed in US'473 is schematically represented as below.

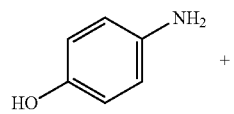

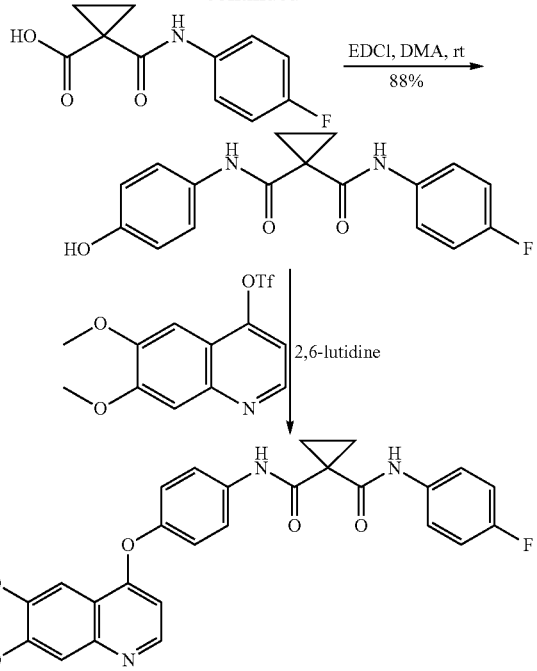

The process disclosed in US'473 involves the use of column chromatography for purification of Cabozantinib which is expensive and time consuming process, hence the process is not suitable for commercial scale. Moreover, the said process involves the use of expensive reagents and solvents and provides Cabozantinib with low yield. Hence, the said process is not suitable for commercial scale.

In view of this, there is a need in the art to develop an alternate process for the preparation of Cabozantinib with high yield & purity and also suitable for commercial scale.

The present invention relates to an improved process for the preparation of Cabozantinib which avoids the usage of expensive reagents and solvents and also column chromatography and provides the Cabozantinib with high yield and purity which is suitable for commercial scale process.

BRIEF DESCRIPTION OF THE INVENTION

The first aspect of the present invention is to provide a process for the preparation of 1-[(4-fluorophenyl)carbamoyl]cyclopropanecarboxylic acid compound of formula-2.

The second aspect of the present invention is to provide an improved process for the preparation of Cabozantinib compound of formula-1.

The third aspect of the present invention is to provide an improved process for the preparation of Cabozantinib (S)-malate compound of formula-1a.

Advantages of the Invention

The present invention avoids the usage of expensive reagents & solvents and column chromatography techniques.

The present invention involves the usage of low cost reagents and solvents which decreases the cost of production and suitable for the commercial scale process.

The process of the present invention provides Cabozantinib (S)-malate with high yield and purity.

DETAILED DESCRIPTION OF THE INVENTION

The term "suitable solvent" used in the present invention refers to "hydrocarbon solvents" selected from aliphatic hydrocarbon solvents such as n-hexane, n-heptane, cyclohexane, petroleum ether and aromatic hydrocarbon solvents such as benzene, toluene, xylene and the like; "ether solvents" such as dimethyl ether, diisopropyl ether, diethyl ether, methyl tert-butyl ether, 1,2-dimethoxy ethane, tetrahydrofuran, 1,4-dioxane, monoxime, dioxime and the like; "ester solvents" such as methyl acetate, ethyl acetate, isopropyl acetate, n-butyl acetate and the like; "polar-aprotic solvents such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol and the like; "polar solvents" such as water or mixtures thereof.

As used herein the present invention, the term "antisolvent" refers to a solvent which is used to precipitate the solid from a solution.

As used herein the present invention the term "suitable base" refers to "alkali metal carbonates" such as sodium carbonate, potassium carbonate, lithium carbonate and the like; "alkali metal bicarbonates" such as sodium bicarbonate, potassium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, sodium tert·butoxide, potassium tert·butoxide, lithium tert·butoxide and the like; alkali metal hydrides such as sodium hydride, potassium hydride, lithium hydride and the like; alkali metal amides such as sodium amide, potassium amide, lithium amide and the like; and organic bases like dimethylamine, diethylamine, diisopropylamine, diisopropylethylamine, diisobutylamine, triethylamine, pyridine, 4-dimethylaminopyridine (DMAP), N-methyl morpholine (NMM), 2,6-lutidine, lithium diisopropylamide; organosilicon bases such as lithium hexamethyldisilazide (LiHMDS), sodium hexamethyldisilazide (NaHMDS), potassium hexamethyldisilazide (KHMDS) or mixtures thereof.

The first aspect of the present invention is to provide a process for the preparation of 1-[(4-fluorophenyl)carbamoyl]cyclopropanecarboxylic acid compound of formula-2, comprising of treating the methyl 1-(4-fluorophenylcarbamoyl) cyclopropanecarboxylate compound of formula-3 with a suitable base in a suitable solvent to provide 1-[(4-fluorophenyl)carbamoyl]cyclopropanecarboxylic acid compound of formula-2.

Wherein the suitable base used is inorganic base selected from "alkali metal hydroxides" such as sodium hydroxide, potassium hydroxide, lithium hydroxide and the like; and the suitable solvent is "polar solvents" such as water.

The preferred embodiment of the present invention provides a process for the preparation of 1-[(4-fluorophenyl)carbamoyl]cyclopropanecarboxylic acid compound of formula-2, comprising of treating the methyl 1-(4-fluorophenylcarbamoyl) cyclopropanecarboxylate compound of formula-3 with potassium hydroxide in water provides 1-[(4-fluorophenyl)carbamoyl]cyclopropanecarboxylic acid compound of formula-2.

The second aspect of the present invention is to provide an improved process for the preparation of Cabozantinib compound of formula-1, comprising of:

a) Reacting 4-chloro-6,7-dimethoxy-quinoline compound of formula-4 with 4-aminophenol in presence of a suitable base in a suitable solvent to provide 4-[(6,7-dimethoxy-4-quinolyl)oxy]aniline followed by treating the obtained compound with hydrochloric acid in a suitable solvent to provide 4-[(6,7-dimethoxy-4-quinolyl)oxy]aniline hydrochloride compound of formula-5, b) reacting the 4-[(6,7-dimethoxy-4-quinolyl)oxy]aniline hydrochloride compound of formula-5 with 1-[(4-fluorophenyl)carbamoyl]cyclopropane carboxylic acid compound of formula-2 in presence of a suitable coupling agent, suitable base and a suitable solvent to provide Cabozantinib base compound of formula-1, c) optionally, purifying the Cabozantinib compound of formula-1 from a suitable solvent to provide pure Cabozantinib base compound of formula-1.

Wherein, in step-a) the suitable base used is "alkali metal alkoxide" such as sodium methoxide, sodium ethoxide, potassium methoxide, potassium ethoxide, sodium tert·butoxide, potassium tert·butoxide, lithium tert·butoxide and the like; the suitable solvent is "polar-aprotic solvent" such as dimethylacetamide, dimethylformamide, dimethylsulfoxide, N-methylpyrrolidone (NMP) and alcoholic solvent such as methanol, ethanol, propanol & isopropanol or the mixtures thereof;

in step-b) the suitable coupling reagent is selected from hydroxybenzotriazole (HOBt), 1-ethyl-3-(3-dimethylaminopropyl)carbodiimide hydrochloride (EDCHCl), benzotriazol-1-yl-oxytripyrrolidinophosphonium hexafluorophosphate (PyBOP), Bromo-trispyrrolidino phosphonium hexafluorophosphate (PyBrOP), 0-(benzotriazol-1-yl)-N,N,N',N'-tetramethyluronium tetrafluoroborate (TBTU), 2-(1H-Benzotriazole-1-yl)-1,1,3,3-tetramethyluronium hexafluorophosphate (HBTU), 1-[bis(dimethylamino)methylene]-1H 1,2,3-triazolo[4,5-b]pyridinium 3-oxid hexafluorophosphate (HATU), 1-cyano-Z-ethoxy-2-oxo-ethylidenaminooxy)dimethylamino-morpholino-carbeniumhexafluorophosphate (COMU) and tetramethyl fluoroformamidinium hexafluorophosphate (TFFH) or mixtures thereof in the presence of a base selected from diisopropyl ethylamine (DIPEA), N-methyl-morpholine (NMM), dimethylaminopyridine (DMAP), pyridine and the like. The suitable solvent used is "chloro solvent" such as dichloromethane, dichloroethane, chloroform, carbon tetrachloride and the like;

in step-c) the suitable solvent is "alcoholic solvent" such as methanol, ethanol, propanol & isopropanol or the mixtures thereof;

The preferred embodiment of the present invention provides an improved process for the preparation of Cabozantinib compound of formula-1, comprising of:

a) Reacting 4-chloro-6,7-dimethoxy-quinoline compound of formula-4 with 4-aminophenol in presence of potassium tert·butoxide in dimethylacetamide provides 4-[(6,7-dimethoxy-4-quinolyl)oxy]aniline followed by treating the obtained compound with hydrochloric acid in methanol provides 4-[(6,7-dimethoxy-4-quinolyl)oxy]aniline hydrochloride compound of formula-5, b) reacting the 4-[(6,7-dimethoxy-4-quinolyl)oxy]aniline hydrochloride compound of formula-5 with 1-[(4-fluorophenyl)carbamoyl]cyclopropane carboxylic acid compound of formula-2 in presence of EDC·HCl and DMAP in dichloromethane provides Cabozantinib base compound of formula-1, c) purifying the Cabozantinib compound of formula-1 from methanol provides pure Cabozantinib base compound of formula-1.

The third aspect of the present invention is to provide an improved process for the preparation of Cabozantinib (S)-malate compound of formula-1a.

a) Treating the cyclopropane-1,1-dicarboxylic acid with thionyl chloride in tetrahydrofuran followed by methanol provides 1-(methoxycarbonyl)cyclopropane carboxylic acid, b) treating the 1-(methoxycarbonyl)cyclopropanecarboxylic acid with thionyl chloride in tetrahydrofuran followed by reacting the obtained compound with 4-fluoroaniline in presence of triethylamine provides methyl 1-(4-fluorophenylcarbamoyl) cyclopropanecarboxylate compound of formula-3, c) treating the compound of formula-3 with a suitable base in a suitable solvent provides 1-[(4-fluorophenyl)carbamoyl]cyclopropane carboxylic acid compound of formula-2, d) reacting 4-chloro-6,7-dimethoxy-quinoline compound of formula-4 with 4-aminophenol in presence of a suitable base in a suitable solvent to provide 4-[(6,7-dimethoxy-4-quinolyl)oxy]aniline followed by treating the obtained compound with hydrochloric acid in a suitable solvent to provide 4-[(6,7-dimethoxy-4-quinolyl)oxy]aniline hydrochloride compound of formula-5, e) reacting the 4-[(6,7-dimethoxy-4-quinolyl)oxy]aniline hydrochloride compound of formula-5 with 1-[(4-fluorophenyl)carbamoyl]cyclopropane carboxylic acid compound of formula-2 obtained in step-(c) in presence of a suitable coupling agent, suitable base and a suitable solvent to provide Cabozantinib base compound of formula-1, f) optionally, purifying the Cabozantinib compound of formula-1 from a suitable solvent to provide pure Cabozantinib base compound of formula-1, g) treating the compound of formula-1 obtained in step(e) or step(f) with L-malic acid in a suitable solvent or mixture of solvents, followed by purifying the obtained compound in a suitable solvent or mixture of solvents to provide pure Cabozantinib (S)-malate compound of formula-1a.

The preferred embodiment of the present invention provides an improved process for the preparation of Cabozantinib (S)-malate compound of formula-1a, comprising of:

a) Treating the cyclopropane-1,1-dicarboxylic acid with thionyl chloride in tetrahydrofuran followed by methanol provides 1-(methoxycarbonyl) cyclopropane carboxylic acid, b) treating the 1-(methoxycarbonyl)cyclopropanecarboxylic acid with thionyl chloride in tetrahydrofuran followed by reacting the obtained compound with 4-fluoroaniline in presence of triethylamine provides methyl 1-(4-fluorophenylcarbamoyl) cyclopropanecarboxylate compound of formula-3, c) treating the compound of formula-3 with potassium hydroxide in water provides 1-[(4-fluorophenyl)carbamoyl] cyclopropanecarboxylic acid compound of formula-2, d) reacting 4-chloro-6,7-dimethoxy-quinoline compound of formula-4 with 4-aminophenol in presence of potassium tert·butoxide in dimethylacetamide provides 4-[(6,7-dimethoxy-4-quinolyl)oxy]aniline followed by treating the obtained compound with hydrochloric acid in methanol provides 4-[(6,7-dimethoxy-4-quinolyl)oxy] aniline hydrochloride compound of formula-5, e) reacting the 4-[(6,7-dimethoxy-4-quinolyl)oxy]aniline hydrochloride compound of formula-5 with 1-[(4-fluorophenyl)carbamoyl]cyclopropane carboxylic acid compound of formula-2 obtained in step-(c) in presence of EDC·HCl and DMAP in dichloromethane provides Cabozantinib base compound of formula-1, f) purifying the Cabozantinib compound of formula-1 from methanol provides pure Cabozantinib base compound of formula-1.

g) treating the compound of formula-1 obtained in step(e) or step(f) with L-malic acid in n-butanol, followed by purifying the obtained compound in a solvent selected from methylisobutylketone (MIBK), n-heptane, methanol, tetrahydrofuran or mixtures thereof provides pure Cabozantinib (S)-malate compound of formula-1a.

PXRD Method of Analysis:

PXRD analysis of the crystalline forms of Cabozantinib or its salts were carried out using Panlytical Expert Pro DY3248 X-ray powder diffractometer using Cu-Ka radiation of 10 wavelength 1.5406 A° and at continuous scan speed of 0.03°/min.

The process for the preparation of Cabozantinib (S)-malate compound of formula-1a is schematically represented as below:

Scheme-I:

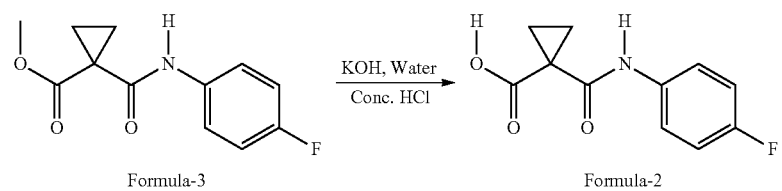

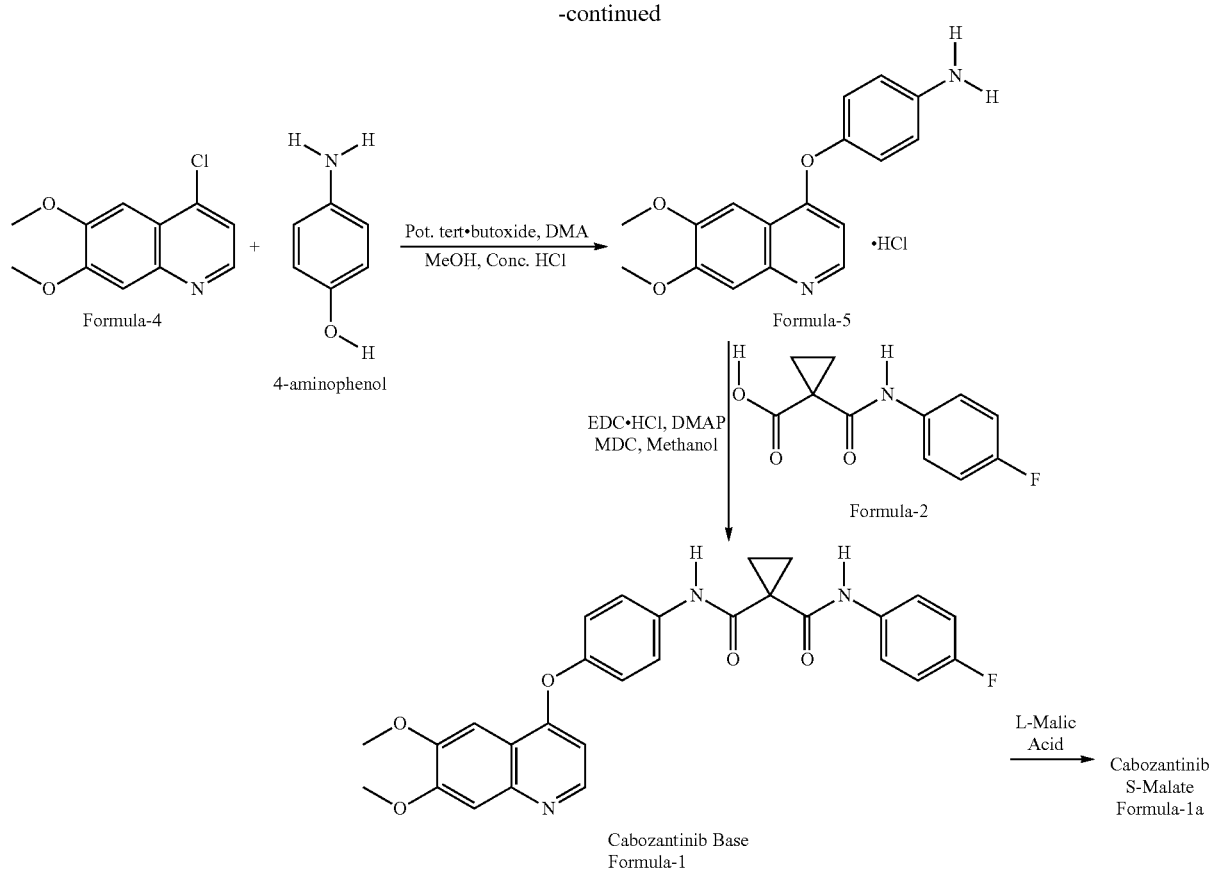

Cabozantinib Base
Formula-1

The best mode of carrying out the present invention was illustrated by the below mentioned examples. These examples are provides as illustration only and hence should not be construed as limitation of the scope of the invention.

EXAMPLES

Example-1: Process for the preparation of 1-[(4-fluorophenyl)carbamoyl]cyclopropanecarboxylic acid Formula-2

Methyl 1-(4-fluorophenyl carbamoyl)cyclopropanecarboxylate compound of formula-3 (300 g) and water (600 mL) were charged into 4N RB flask and stirred for 10 min at 25-35° C. Potassium hydroxide solution (99.12 g of KOH dissolved in 900 mL of water) was slowly added to the reaction mixture and stirred for 4 h at the same temperature to get the clear solution. Water (1500 mL) was added to the reaction mixture and acidified with Conc. HCl (138 mL) followed by stirred for 2 h. Filtered the compound, washed with water and dried to get the title compound.

Yield: 272.27 g (78% by theory). Purity by HPLC: 99.98%.

Example-2: Process for the preparation of 4-[(6,7-dimethoxy-4-quinolyl)oxy]aniline hydrochloride Formula-5

Step-(a): Preparation of Freebase Compound of Formula-5:

N,N-dimethylacetamide (2000 mL) and potassium tertiary butoxide (180.61 g) were charged into 4N RB flask under nitrogen atmosphere, and stirred for 10 min at 25-30° C. 4-aminophenol (175.65 g) was added lot wise to the reaction mixture and stirred for 30 min 4-chloro-6,7-dimethoxy-quinoline compound of formula-4 (200 g) was added to the reaction mixture and heated to 90-95° C. and stirred for 7 h. Cooled the reaction mixture to 25-35° C. Water (2000 mL) was added to the reaction mixture and stirred for 2 h at the same temperature. Filtered and washed the compound with N,N-dimethylacetamide and water to get the freebase compound of formula-5. Methanol (1000 mL) was added to the obtained wet freebase compound of formula-5. Heated the reaction mixture to reflux temperature and stirred for 30 min and then cooled to 25-30° C. Filtered and washed the obtained compound with methanol to get the freebase compound of formula-5. Wet wt: 261.8 g Step-(b): HCl Salt Preparation:

The wet compound obtained in above step-(a) and methanol (1000 mL) were charged in to 4N RB flask and stirred for 10 min at 25-30° C. Conc. HCl (87.27 g) was added to the reaction mixture and stirred for 2 h at the same temperature. Filtered the compound, washed with methanol and dried to get the title compound. Yield: 215.6 g. Purity by HPLC: 99.94%.

Example-3: Process for the Preparation of Cabozantinib Compound of Formula-1

4-[(6,7-dimethoxy-4-quinolyl)oxy]aniline hydrochloride compound of formula-5 (50 g) and dichloromethane (MDC) (750 mL) were charged into 4N RB flask under nitrogen atmosphere and stirred for 5 min at 25-30° C. The 1-[(4- fluorophenyl)carbamoyl]cyclopropanecarboxylic acid compound of formula-2 (36.87 g), dimethylaminopyridine (DMAP) (29.35 g) and N-(3-Dimethylaminopropyl)-N'-ethylcarbodiimide hydrochloride (EDC·HCl) (46 g) were added to the reaction mixture and stirred for 5 h at the same temperature. Water (750 mL) was added to the reaction mixture and further stirred for 2 h at 25-30° C. Filtered, washed the compound with water followed by MDC to get the title compound.

Example-4: Process for the Purification of Cabozantinib Compound of Formula-1

Cabozantinib obtained in example-3 and methanol (700 mL) were charged in 4N RB flask and stirred for 10 min at 25-30° C. Heated the reaction mixture to 60-65° C. and stirred for 30 min. Cooled the reaction mixture to 25-30° C. followed by methanol (350 mL) was added to the reaction mixture and stirred for 3 h at the same temperature. Filtered the compound and washed with methanol and dried to get the title compound. Yield: 56.91 g. Purity by HPLC: 99.45%.

Example-5: Process for the Preparation of Cabozantinib S-Malate Compound of Formula-1a Cabozantinib (20 g) and DMF (60 mL) were charged in 4N RB flask and stirred for 5 min at 25-30° C. Heated the reaction mixture to 50-55° C. to get the clear solution. The obtained solution was treated with charcoal (2 g) and stirred for 30 min. Filtered the compound and washed with DMF. Charged the obtained filter ML's in to 4N RB flask and heated to 50-55° C. The L-malic solution [6.4 g of L-malic acid dissolved in 8 mL of water] was added to the reaction mixture and stirred for 5 min at the same temperature. A mixture of acetone (280 mL) and methanol (120 mL) was added to the reaction mixture and stirred for 30 min. Cooled the reaction mixture to 25-30° C. and stirred for 17 h at the same temperature. Filtered the compound and washed with a mixture of acetone and methanol and dried to get the title compound. Yield: 12.87 g.

Example-6: Process for the Preparation of Crystalline Form N-2 of Cabozantinib S-Malate Compound of Formula-1a Cabozantinib (20 g) and n-Butanol (800 mL) were charged into 4N RB flask and stirred for 5 min at 25-30° C. Heated the reaction mixture to 95-100° C. and stirred for 20 min to get the clear solution. The obtained solution was treated with charcoal (2 g) and stirred for 30 min at 80-85° C. Filtered the compound and washed with n-Butanol. Charged the obtained filter ML's into 4N RB flask and heated to 70-75° C. Charged L-malic acid (6.66 g) and stirred for 5 min Cooled the reaction mixture temperature to 25-30° C. and stirred for 2 h at the same temperature. Filtered the compound and washed with n-Butanol. Wet wt.: 65.75 g The obtained above wet compound and MIBK (400 mL) were charged into 4N RB flask and stirred for 2 h at 25-30° C. Filtered the compound and washed with MIBK and dried to get the title compound. Yield: 18.89 g.

Example-7: Process for the Preparation of Crystalline Form N-2 of Cabozantinib S-Malate Compound of Formula-1a Cabozantinib (20 g) and n-Butanol (800 mL) were charged into 4N RB flask and stirred for 5 min at 25-30° C. Heated the reaction mixture to 95-100° C. and stirred for 20 min to get the clear solution. The obtained solution was treated with charcoal (2 g) and stirred for 30 min at 80-85° C. Filtered the compound and washed with n-Butanol. Charged the obtained filter ML's into 4N RB flask and heated to 70-75° C. Charged L-malic acid (6.66 g) and stirred for 10 min. Cooled the reaction mixture temperature to 25-30° C. and stirred for 2 h at the same temperature. Filtered the compound and washed with n-Butanol. Wet wt.: 73.51 g The obtained above wet compound and n-Heptane (400 mL) were charged into 4N RB flask and stirred for 2 h at 25-30° C. Filtered the compound and washed with n-Heptane and dried to get the title compound. Yield: 16.8 g.

Example-8: Process for the Preparation of Crystalline Form N-2 of Cabozantinib S-Malate Compound of Formula-1a Cabozantinib (20 g) and n-Butanol (800 mL) were charged into 4N RB flask and stirred for 5 min at 25-30° C. Heated the reaction mixture to 95-100° C. and stirred for 20 min to get the clear solution. The obtained solution was treated with charcoal (2 g) and stirred for 30 min at 80-85° c. Filtered the compound and washed with n-Butanol. Charged the obtained filter ML's into 4N RB flask and heated to 70-75° C. The L-malic acid solution [6.66 g of L-malic acid dissolved in 33 mL of n-Butanol at 60° C.] was added to the reaction mixture and stirred for 15 min at same temperature. Cooled the reaction mixture temperature to 25-30° C. and stirred for 2 h. Filtered the compound and washed with n-Butanol. Wet wt.: 68.46 g The obtained above wet compound and methanol (400 mL) were charged into 4N RB flask and stirred for 2 h at 25-30° C. Filtered the compound and washed with methanol and dried to get the title compound. Yield: 12.79 g.

Example-9: Process for the Preparation of Crystalline Form N-2 of Cabozantinib S-Malate Compound of Formula-1a Cabozantinib (20 g) and n-Butanol (800 mL) were charged into 4N RB flask and stirred for 5 min at 25-30° C. Heated the reaction mixture to 95-100° C. and stirred for 20 min to get the clear solution. The obtained solution was treated with charcoal (2 g) and stirred for 30 min at 80-85° c. Filtered the compound and washed with n-Butanol. Charged the obtained filter ML's into 4N RB flask and heated to 70-75° C. The L-malic acid solution [6.66 g of L-malic acid dissolved in 33 mL of n-Butanol at 40° C.] was added to the reaction mixture and stirred for 15 min at same temperature. Cooled the reaction mixture temperature to 25-30° C. and stirred for 2 h. Filtered the compound and washed with n-Butanol. Wet wt.: 67.23 g The obtained above wet compound and MIBK (400 mL) were charged into 4N RB flask and stirred for 2 h at 25-30° C. Filtered the compound and washed with MIBK and dried to get the title compound. Yield: 16.4 g.

Example-10: Process for the Preparation of Crystalline Form N-2 of Cabozantinib S-Malate Compound of Formula-1a Cabozantinib (60 g) and n-Butanol (2400 mL) were charged into 4N RB flask and stirred for 10 min at 25-30° C. Heated the reaction mixture to 95-100° C. and stirred for 20 min to get the clear solution. The obtained solution was treated with charcoal (2 g) and stirred for 30 min at 80-85° C. Filtered the compound and washed with n-Butanol. Charged the obtained filter ML's into 4N RB flask and heated to 70-75° C. Charged the obtained filter ML's into 4N RB flask and heated to 70-75° C. Charged L-malic acid (20 g) and stirred for 5 min at same temperature. Cooled the reaction mixture temperature to 25-30° C. and stirred for 2 h at the same temperature. Filtered the compound and washed with n-Butanol. Wet wt.: 197.5 g The obtained above wet compound and methanol (1200 mL) were charged into 4N RB flask and stirred for 2 h at 25-30° C. Filtered the compound and washed with Methanol and dried to get the title compound. Yield: 47.0 g.

The PXRD pattern of compound of formula-1a obtained from examples 6-10 are matching with the PXRD of crystalline Form N-2 of Cabozantinib (S)-malate disclosed in U.S. Pat. No. 8,877,776B2 herein incorporated for reference.

We claim:

1. A process for the preparation of Cabozantinib (formula-1),

Formula-1

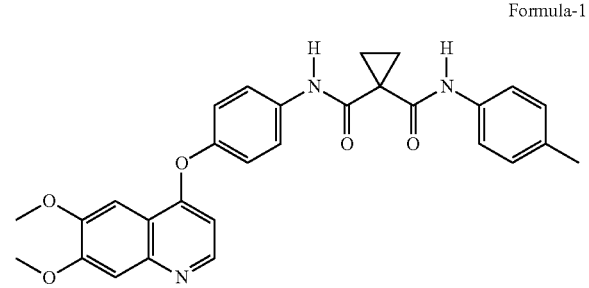

comprising:

a) Reacting 4-chloro-6,7-dimethoxy-quinoline (formula-4),

Formula-4

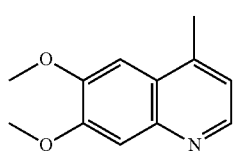

with 4-aminophenol in the presence of a suitable base in a suitable solvent to provide 4-[(6,7-dimethoxy-4-quinolyl)oxy]aniline followed by treating the obtained compound with hydrochloric acid in a suitable solvent to provide 4-[(6,7-dimethoxy-4-quinolyl)oxy]aniline hydrochloride (formula-5), Formula-5

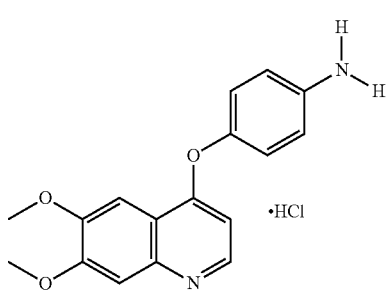

b) reacting the resulting 4-[(6,7-dimethoxy-4-quinolyl)oxy]aniline hydrochloride (formula-5) with 1-[(4-fluorophenyl)carbamoyl]cyclopropane carboxylic acid (formula-2), Formula-2

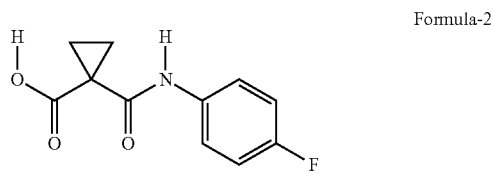 [SMILES: O=C(O)C1(C(=O)Nc2ccc(F)cc2)CC1]

in the presence of a suitable coupling agent, suitable base and a suitable solvent to provide Cabozantinib (formula-1), c) optionally, purifying the resulting Cabozantinib (formula-1) from a suitable solvent to provide pure Cabozantinib (formula-1).

2. The process of claim-1, wherein, in step-a) the suitable base used is "alkali metal alkoxide";

in step-b) the suitable coupling reagent is selected from hydroxybenzotriazole (HOBt), 1-ethyl-3-(3-dimethylaminopropyl)carbodiimide hydrochloride (EDCHCl), benzotriazol-1-yl-oxytripyrrolidinophosphonium hexafluorophosphate (PyBOP), Bromo-trispyrrolidino phosphonium hexafluorophosphate (PyBrOP), 0-(benzotriazol-1-yl)-N,N,N',N'-tetramethyluronium tetrafluoroborate (TBTU), 2-(1H-Benzotriazole-1-yl)-1,1,3,3-tetramethyluronium hexafluorophosphate (HBTU), 1-[bis(dimethylamino) methylene]-1H 1,2,3-triazolo[4,5-b]pyridinium 3-oxid hexafluorophosphate (HATU), 1-cyano-Z-ethoxy-2-oxoethylidenaminooxy) dimethylamino-morpholino-carbeniumhexafluorophosphate (COMU) and tetramethyl fluoroformamidinium hexafluorophosphate (TFFH) or mixtures thereof in the presence of a base selected from diisopropyl ethylamine (DIPEA), N-methyl-morpholine (NMM), dimethylaminopyridine (DMAP) and pyridine; the suitable solvent used is "chloro solvent";

in step-c) the suitable solvent is "alcoholic solvent".

3. The process of claim 1, wherein the process comprises:

a) Reacting 4-chloro-6,7-dimethoxy-quinoline (formula-4) with 4-aminophenol in the presence of potassium tert-butoxide in dimethylacetamide to provide 4-[(6,7-dimethoxy-4-quinolyl)oxy]aniline followed by treating the obtained compound with hydrochloric acid in methanol to provide 4-[(6,7-dimethoxy-4-quinolyl)oxy] aniline hydrochloride (formula-5), b) reacting the 4-[(6,7-dimethoxy-4-quinolyl)oxy]aniline hydrochloride (formula-5) with 1-[(4-fluorophenyl)carbamoyl]cyclopropane carboxylic acid (formula-2)

in the presence of EDC-HCl and DMAP in dichloromethane to provide Cabozantinib (formula-1), c) purifying the Cabozantinib (formula-1) from methanol to provide pure Cabozantinib (formula-1).

4. The process of claim 1, wherein the process further comprises a step of preparing the 1-[(4-fluorophenyl)carbamoyl]cyclopropane carboxylic acid (formula-2) used in step b), comprising:

treating methyl 1-(4-fluorophenylcarbamoyl) cyclopropanecarboxylate (formula-3),

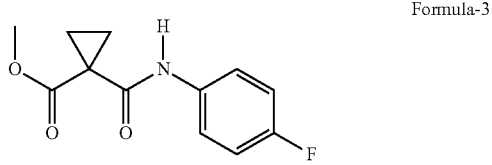 [SMILES: COC(=O)C1(C(=O)Nc2ccc(F)cc2)CC1]

Formula-3 with potassium hydroxide in water to provide 1-[(4-fluorophenyl)carbamoyl] cyclopropane carboxylic acid (formula-2).

5. A process for the preparation of 4-[(6,7-dimethoxy-4-quinolyl)oxy]aniline hydrochloride (formula-5), comprising reacting 4-chloro-6,7-dimethoxy-quinoline(formula-4) with 4-aminophenol in the presence of potassium tert-butoxide in dimethylacetamide to provide 4-[(6,7-dimethoxy-4-quinolyl)oxy]aniline, followed by treating the obtained compound with hydrochloric acid in methanol to provide 4-[(6,7-dimethoxy-4-quinolyl)oxy] aniline hydrochloride (formula-5).

6. A process for the preparation of Cabozantinib (formula-1), comprising reacting 4-[(6,7-dimethoxy-4-quinolyl)oxy] aniline hydrochloride (formula-5) with 1-[(4-fluorophenyl) carbamoyl]cyclopropane carboxylic acid (formula-2) in the presence of EDC-HCl and DMAP in dichloromethane to provide Cabozantinib (formula-1).

7. The process of claim 1, wherein the process is a process for the preparation of Cabozantinib (S)-malate, and the process comprises:

i) Treating cyclopropane-1,1-dicarboxylic acid with thionyl chloride in tetrahydrofuran followed by methanol to provide 1-(methoxycarbonyl)cyclopropane carboxylic acid, ii) treating the 1-(methoxycarbonyl)cyclopropanecarboxylic acid with thionyl chloride in tetrahydrofuran followed by reacting the obtained compound with 4-fluoroaniline in the presence of triethylamine to provide methyl 1-(4-fluorophenylcarbamoyl) cyclopropanecarboxylate (formula-3), iii) treating the compound of formula-3 with a suitable base in a suitable solvent to provide 1-[(4-fluorophenyl)carbamoyl]cyclopropane carboxylic acid (formula-2), a) reacting 4-chloro-6,7-dimethoxy-quinoline (formula-4) with 4-aminophenol in the presence of a suitable base in a suitable solvent to provide 4-[(6,7-dimethoxy-4-quinolyl)oxy]aniline, followed by treating the obtained compound with hydrochloric acid in a suitable solvent to provide 4-[(6,7-dimethoxy-4-quinolyl)oxy]aniline hydrochloride (formula-5), b) reacting the 4-[(6,7-dimethoxy-4-quinolyl)oxy]aniline hydrochloride (formula-5) with the 1-[(4-fluorophenyl) carbamoyl]cyclopropane carboxylic acid (formula-2) obtained in step-(iii) in the presence of a suitable coupling agent, suitable base and a suitable solvent to provide Cabozantinib (formula-1), c) optionally, purifying the Cabozantinib (formula-1) from a suitable solvent to provide pure Cabozantinib (formula-1), d) treating the compound of formula-1 obtained in step-(b) or step-(c) with L-malic acid in a suitable solvent or mixture of solvents, followed by purifying the obtained compound in a suitable solvent or mixture of solvents to provide pure Cabozantinib (S)-malate.

8. The process of claim 7, wherein the process comprises:

i) Treating the cyclopropane-1,1-dicarboxylic acid with thionyl chloride in tetrahydrofuran followed by methanol to provide 1-(methoxycarbonyl)cyclopropane carboxylic acid, ii) treating the 1-(methoxycarbonyl)cyclopropanecarboxylic acid with thionyl chloride in tetrahydrofuran followed by reacting the obtained compound with 4-fluoroaniline in the presence of triethylamine to provide methyl 1-(4-fluorophenylcarbamoyl) cyclopropanecarboxylate (formula-3), iii) treating the compound of formula-3 with potassium hydroxide in water to provide 1-[(4-fluorophenyl)carbamoyl]cyclopropanecarboxylic acid (formula-2), a) reacting the 4-chloro-6,7-dimethoxy-quinoline (formula-4) with 4-aminophenol in the presence of potassium tert-butoxide in dimethylacetamide to provide 4-[(6,7-dimethoxy-4-quinolyl)oxy]aniline, followed by treating the obtained compound with hydrochloric acid in methanol to provide 4-[(6,7-dimethoxy-4-quinolyl) oxy] aniline hydrochloride (formula-5), b) reacting the 4-[(6,7-dimethoxy-4-quinolyl)oxy]aniline hydrochloride (formula-5) with the 1-[(4-fluorophenyl) carbamoyl]cyclopropane carboxylic acid (formula-2) obtained in step-(iii) in the presence of EDC-HCl and DMAP in dichloromethane to provide Cabozantinib (formula-1), c) purifying the Cabozantinib (formula-1) from methanol to provide pure Cabozantinib (formula-1), d) treating the compound of formula-1 obtained in step-(c) with L-malic acid in n-butanol, followed by purifying the obtained compound in a solvent selected from methylisobutylketone (MIBK), n-heptane, methanol, tetrahydrofuran or mixtures thereof, to provide pure Cabozantinib (S)-malate.

\* \* \* \* \*